United States Patent [19]

Raaf et al.

[11] Patent Number: 4,743,442

[45] Date of Patent: May 10, 1988

[54] SKIN CARE COMPOSITION

[75] Inventors: Helmut Raaf, Bockenau; Rudolf Bimczok, Mainz-Finthen; Ingrid Ittel, Ingelheim, all of Fed. Rep. of Germany

[73] Assignee: Blendax-Werke R. Schneider GmbH & Co., Mainz, Fed. Rep. of Germany

[21] Appl. No.: 802,388

[22] Filed: Nov. 27, 1985

Related U.S. Application Data

[63] Continuation of Ser. No. 630,402, Jul. 13, 1984, abandoned.

[30] Foreign Application Priority Data

Aug. 2, 1983 [DE] Fed. Rep. of Germany ....... 3327840

[51] Int. Cl.$^4$ .................. A61K 7/40; A61K 7/42; A61K 7/48; A61K 9/12
[52] U.S. Cl. ........................... 424/47; 424/59; 424/60; 514/167; 514/251; 514/275; 514/356; 514/419; 514/458; 514/474; 514/725; 514/773; 514/783; 514/844; 514/847; 514/873; 514/887; 514/938; 514/939; 514/944; 514/945
[58] Field of Search ................ 424/59, 47, 60; 514/844

[56] References Cited

U.S. PATENT DOCUMENTS

| | | | |
|---|---|---|---|
| 711,263 | 10/1902 | Robertson | 424/DIG. 4 |
| 2,268,736 | 1/1942 | Buxton et al. | 424/70 |
| 2,276,531 | 3/1942 | Wechsler et al. | 424/70 |
| 4,309,411 | 1/1982 | Toida | 424/63 |

FOREIGN PATENT DOCUMENTS

| | | | |
|---|---|---|---|
| 1045035 | 12/1978 | Canada | 424/59 |
| 1945458 | 11/1970 | Fed. Rep. of Germany | 424/358 |
| 2124735 | 11/1972 | Fed. Rep. of Germany | 424/358 |
| 2498451 | 7/1982 | France | 514/179 |
| 51-57835 | 5/1976 | Japan | 424/366 |
| 55-87714 | 7/1980 | Japan | 274/59 |
| 132377 | 9/1919 | United Kingdom | 424/44 |
| 423426 | 1/1935 | United Kingdom | 424/148 |
| 868283 | 5/1961 | United Kingdom | 514/179 |

*Primary Examiner*—Dale R. Ore
*Attorney, Agent, or Firm*—Birch, Stewart, Kolasch & Birch

[57] ABSTRACT

Skin care composition containing mineral salts releasing sodium, potassium, megnesium, calcium and zinc salts in defined concentration, and, optionally, compounds releasing copper, manganese, vanadium, aluminum, cobalt and/or iron ions.

13 Claims, No Drawings

SKIN CARE COMPOSITION

This application is a continuation of copending application Ser. No. 630,402, filed on July 13, 1984, now abandoned.

The present invention relates to compositions for skin care with excellent properties.

When using skin care preparations, especially skin creams and lotions, the customer expects that these preparations may be distributed well on the skin surface, will penetrate quickly into the skin without leaving an unpleasant oily or fatty coating and, moreover, after treatment the skin should have a smooth and soft feeling.

From good skin care preparations, a longlasting effect is to be expected, i.e., active ingredients contained therein should penetrate into the epidermis and effect a regeneration of the horny layers.

To solve this problem, plenty of active ingredients were proposed in this respect. First of all, moisture regulating additives play an important role, especially the imitation of the so-called NMF-(Natural Moisturizing Factor) Factor.

Also vitamins, amino acids, hydroxy- and polycarboxylic acids, polyalcohols, urea, different plant extracts, hyperemizing and blood flow promoting agents have been used to improve the skin condition.

It is also known from the prior art that different mineralizing compounds are important for keeping the skin in a healthy condition. These mineralizing compounds are used as co-enzymes and bio-catalysts, for regulation of water equivalence and osmotic pressure, for keeping the pH-values constant and to hold up bio-electrical potentials.

Therefore it has also been proposed to administer such mineralizing compounds alone or in combination by systemic application to keep the skin in healthy condition (see, e.g. M. Haas, Cosmetic Journal of Aug. 5, 1982, p. 8–9).

It has now been found, and that is the object of the present invention, it by a special, qualitatively and quantitatively exactly defined selection of different mineral salts an excellent skin care effect may be obtained in skin care compositions even by local application.

An object of the present invention is a skin care composition, containing, besides the usual carrier agents, a mixture of compounds releasing cations in the following proportions (calculated on the corresponding ions):

Sodium: 0,01–5,0% by weight, especially 0,1 to 2,5% by weight;
potassium: 0,01–3,0% by weight, especially 0,1 to 1,5% by weight;
magnesium: 0,01–2,0% by weight, especially 0,1 to 1,0% by weight;
calcium: 0,01–2,0% by weight, especially 0,1 to 1,0% by weight;
zinc: 0,01–1,0% by weight, especially 0,05 to 0,5% by weight;

and, optionally, copper: 0,0001–0,01% by weight, especially 0,0005 to 0,005% by weight, calculated on the total composition of the skin care composition.

According to a preferred embodiment of the invention the skin care composition contains additional mineral salts releasing the following ions in the cited amounts:

Manganese: 0,0001–0,01% by weight, especially 0,001–0,005% by weight;
iron: 0,001–0,01% by weight, especially 0,001–0,005% by weight;
vanadium: 0,0001–0,01% by weight, especially 0,001–0,005% by weight;
aluminium: 0,0001–0,5% by weight, especially 0,01–0,1% by weight;

and/or cobalt: 0,0001–0,01% by weight, especially 0,001–0,005% by weight, calculated on the total composition of the preparation.

According to the present invention, these ions are applied as physiologically compatible mineral salts in suitable concentrations.

Examples for such salts are the chlorides, sulphates, phosphates, citrates, lactates, glycerophosphates, gluconates, edetates, tartrates, malates, mandelates, benzoates, salicylates, phytates, cinnamates, or amino acid salts. Principally every salt of those elements is suitable for releasing ions in the defined amounts in the skin care compositions according to the invention.

In addition to the mineralizing mixtures according to the invention, the skin care compositions may contain additional active ingredients known per se.

Such active ingredients are especially different vitamins well-known for skin care like the vitamins A, $B_1$, $B_2$, $B_6$, $B_{12}$, D, E, K, H, folic acid, nicotinamide and pantothenic acid and D-panthenol. Especially preferred are vitamin A, vitamin E (tocopherol), and D-panthenol.

A further, well-known group of active ingredients which may be used in the skin care composition according to the invention are amino acids like methionine, cystine, cysteine, alanine, asparagic acid, leucine, isoleucine, lysine, valine, serine, arginine, glutamic acid, phenylalanine, threonine, tyrosine and tryptophane. Suitable are also protein hydrolyzates with low molecular weight.

If the skin care compositions according to the invention are to be used as sun care agents, they should contain substances absorbing UV-radiation.

A further group of suitable active ingredients to be used in addition to the mineralizing mixtures according to the invention are different plant extracts, blood flow promoting compounds, anti-inflammatory agents, etc.

In general it can be stated that, in addition to the synergistic mixture of mineral salts in the skin care composition according to the invention, all physiologically compatible compounds proposed for skin care up to now may be used, however, they have to be compatible with the other compounds of the corresponding composition.

The skin care compositions according to the present invention can be used in any application form suitable for skin cosmetics. Preferred are skin creams which may be applied as oil-in-water emulsions or water-in-oil emulsions which are prepared from the well-known carriers and additives.

However, also lotions, gels or solutions such as skin or face waters and lotions may be used as carriers for the skin care compositions according to the invention.

Those compositions may also be prepared as aerosol sprays by addition of usual propellents.

It is also possible to apply face packs or face masks, pastes or suspensions.

The composition and preparation of such carriers are well-known for the artisan and described in detail in the different cosmetic handbooks and monographies. As an example, the handbook of K. Schrader, "Grundlagen und Rezepturen der Kosmetika" (1979, Dr. Alfred Hüthig Verlag, Heidelberg) may be cited, especially p. 227–375.

The pH-values of the skin care compositions according to the present invention are preferably between 4 and 8; an especially suitable pH-value for application on the skin is between 4 and 6.

The following examples 1 to 9 show illustrative compositions of skin care agents according to the invention. The percentages are related to percent by weight.

EXAMPLE 1

Skin cream for dry skin

| | |
|---|---|
| Silicone oil | 11,50% |
| Collagen hydrolyzate | 0,50% |
| Isopropyl myristate | 2,00% |
| Glycol distearate | 2,00% |
| White oil | 10,00% |
| Cetyl alcohol | 3,50% |
| Oleyl oleate | 4,00% |
| Glycerol mono-/polyoxyethylene stearate | 4,00% |
| Ethoxylated fatty alcohol | 1,00% |
| Almond oil | 6,00% |
| Glycerol | 4,00% |
| Thickener | 0,50% |
| Preservative | 0,55% |
| Vitamin A (200,000 I.U.) | 0,05% |
| Vitamin E | 0,05% |
| D-Panthenol | 0,50% |
| Perfume | 0,40% |
| Sodium chloride | 0,20% |
| Potassium chloride | 0,10% |
| Calcium chloride.2 $H_2O$ | 0,0375% |
| Zinc sulphate.7 $H_2O$ | 0,025% |
| Magnesium sulphate.7 $H_2O$ | 0,05% |
| Copper sulphate.5 $H_2O$ | 0,0037% |
| Ammonium vanadate | 0,0012% |
| Manganese sulphate.$H_2O$ | 0,00015% |
| Demineralized water | ad 100% |
| pH-value: about 4,5 | |

EXAMPLE 2

Face cream for normal skin

| | |
|---|---|
| Oleyl oleate | 3,00% |
| Silicone oil | 1,50% |
| White oil | 5,00% |
| Purcellin oil | 3,50% |
| Cetyl palmitate | 2,50% |
| Stearyl alcohol | 3,50% |
| Glycol distearate | 2,00% |
| Sorbitan monooleate | 2,00% |
| Sorbitan polyoxyethylene stearate | 2,00% |
| Polyglycol ether | 1,00% |
| Glycerol | 3,00% |
| Perfume | 0,40% |
| Preservative | 0,35% |
| Thickener | 0,50% |
| Vitamin A (200,000 I.U.) | 0,05% |
| Vitamin E | 0,05% |
| D-Panthenol | 0,50% |
| Sodium chloride | 0,25% |
| Potassium chloride | 0,15% |
| Calcium chloride.$H_2O$ | 0,04% |
| Zinc sulphate.7 $H_2O$ | 0,02% |
| Magnesium sulphate.7 $H_2O$ | 0,05% |
| Copper sulphate.5 $H_2O$ | 0,004% |
| Manganese sulphate.$H_2O$ | 0,0002% |
| Demineralized water | ad 100% |
| pH-value: about 4,5 | |

EXAMPLE 3

Hand lotion

| | |
|---|---|
| Glycerol monostearate | 4,00% |
| 2-Ethylhexyl palmitate | 17,00% |
| Sorbitol (60%) | 4,00% |
| Silicone oil | 0,75% |
| Purcellin oil | 3,00% |
| Sorbitan polyoxyethylene stearate | 2,00% |
| Perfume | 0,45% |
| Polyglycol ether | 1,20% |
| Amino acids mixture | 0,80% |
| Sodium chloride | 0,25% |
| Potassium chloride | 0,10% |
| Magnesium chloride | 0,10% |
| Calcium chloride.2 $H_2O$ | 0,05% |
| Zinc chloride | 0,03% |
| Copper chloride | 0,005% |
| Ferrons (II) sulphate.2 $H_2O$ | 0,001% |
| Aluminum sulphate | 0,05% |
| Preservative | 0,30% |
| Water | ad 100% |

EXAMPLE 4

Moisturizing lotion

| | |
|---|---|
| Polyoxyethylene fatty acid ester | 5,50% |
| Glycerol sorbitan fatty acid ester | 2,50% |
| Isopropyl myristate | 4,00% |
| Decyl oleate | 4,00% |
| Fatty acid esters (PCL -liquid) | 4,00% |
| 2-Octyl dodecanol | 2,00% |
| Perhydrosqualene | 8,00% |
| Glycerol | 2,00% |
| 1,2-Propylenglycol | 1,80% |
| Urea | 2,00% |
| Amino acid complex | 0,50% |
| Perfume | 0,40% |
| Preservative | 0,25% |
| Sodium lactate | 1,00% |
| Magnesium sulphate.7 $H_2O$ | 0,80% |
| Potassium citrate.$H_2O$ | 0,90% |
| Zinc citrate.2 $H_2O$ | 0,35% |
| Calcium gluconate.$H_2O$ | 0,50% |
| Copper salicylate.4 $H_2O$ | 0,005% |
| Water | ad 100% |

EXAMPLE 5

Sun protective cream

| | |
|---|---|
| Cetyl alcohol | 17,50% |
| Polyoxyethylene sorbitan lanolate | 4,00% |
| Sorbitan monolaurate | 2,50% |
| Polyoxyethylene sorbitan monolaurate | 6,00% |
| 2-Ethoxyethyl p-methoxycinnamate | 2,50% |
| Glycerol | 3,50% |
| Preservative | 0,25% |
| Perfume | 0,50% |
| Sodium chloride | 0,50% |
| Potassium chloride | 0,50% |
| Magnesium sulphate.7 $H_2O$ | 0,70% |
| Zinc citrate.2 $H_2O$ | 0,20% |
| Calcium chloride.2 $H_2O$ | 0,20% |
| Copper sulphate.5 $H_2O$ | 0,005% |
| Cobalt (II) chloride.2 $H_2O$ | 0,0005% |
| Aluminum chloride.6 $H_2O$ | 0,02% |
| Manganese chloride.4 $H_2O$ | 0,003% |
| Iron (III) chloride.6 $H_2O$ | 0,005% |
| Water | ad 100% |

EXAMPLE 6

Body lotion

| | |
|---|---|
| Polyoxyethylene oleyl ether (2 EO groups) | 2,50% |
| Polyoxyethylene oleyl ether (20 EO groups) | 4,50% |
| Lanolin alcohols (Lipocol$^R$) | 3,00% |
| Beeswax | 5,00% |
| Isopropyl isostearate | 12,00% |
| Cetyl alcohol | 6,00% |
| Silicone oil | 0,30% |
| Glycerol | 3,50% |
| Preservative | 0,35% |
| Perfume | 0,40% |
| Protein hydrolyzate | 0,60% |
| Sodium dihydrogen phosphate.2 $H_2O$ | 1,00% |
| Potassium monohydrogenphosphate | 0,75% |
| Calcium glycerophosphate | 0,80% |
| Magnesium citrate.5 $H_2O$ | 0,65% |
| Zinc lactate.2 $H_2O$ | 0,20% |
| Copper lactate.2 $H_2O$ | 0,01% |
| Manganese nitrate.4 $H_2O$ | 0,001% |
| D-Panthenol | 0,10% |
| Vitamin B6 (Hydrochloride) | 0,10% |
| Vitamin E (Tocopherol acetate) | 0,10% |
| Vitamin F | 0,25% |
| Water | ad 100% |

EXAMPLE 7

Face lotion

| | |
|---|---|
| Ethanol | 8,00% |
| 1-Methoxypropanol(-2) | 7,00% |
| Hamamelis extract | 0,50% |
| Ester of hydrogenated castor oil fatty acid with oxethylated glycerol | 0,30% 0,30% |
| D-Panthenol | 0,50% |
| Lactic acid | 0,50% |
| Aluminum lactate | 0,50% |
| Sodium lactate | 1,20% |
| Potassium benzoate.3 $H_2O$ | 0,50% |
| Zinc chloride | 0,25% |
| Magnesium lactate.3 $H_2O$ | 0,30% |
| Calcium chloride.2 $H_2O$ | 0,60% |
| Copper sulphate.5 $H_2O$ | 0,005% |
| Manganese chloride.4 $H_2O$ | 0,005% |
| Iron (III) chloride | 0,005% |
| Perfume | 0,15% |
| Water | ad 100% |

EXAMPLE 8

Gel for skin care and protection

| | |
|---|---|
| Sodium alginate | 1,80% |
| Sorbitol, 60% | 5,00% |
| DL-Serin | 0,50% |
| Amino acid complex | 1,00% |
| Vitamin A, water-soluble | 0,50% |
| Urea | 2,00% |
| Polyvinyl pyrrolidone | 2,00% |
| Glucose | 1,00% |
| Preservative | 0,20% |
| Perfume oil | 0,20% |
| Sodium chloride | 1,00% |
| Potassium chloride | 1,00% |
| Magnesium chloride.6 $H_2O$ | 0,70% |
| Calcium chloride.2 $H_2O$ | 0,85% |
| Zinc sulphate.7 $H_2O$ | 0,20% |
| Copper sulphate.5 $H_2O$ | 0,01% |
| Manganese. $H_2O$ | 0,005% |
| Sodium metavanadate | 0,005% |

-continued

| | |
|---|---|
| Water | ad 100% |

EXAMPLE 9

Foam mask

| | |
|---|---|
| Cetylstearyl alcohol | 2,80% |
| Cetylstearyl sulphate, sodium salt | 4,00% |
| Mixture of mono-, di- and tri (alkyl-tetraglycolether) orthophosphoric acid ester (Hostaphat$^R$ KW 340) | 2,80% |
| Ethanol | 3,50% |
| Sorbitol, 60% | 2,00% |
| Isopropyl myristate | 3,20% |
| Allantoin | 0,10% |
| Preservative | 0,20% |
| Perfume | 0,20% |
| Sodium lactate | 1,20% |
| Potassium vanadium sulphate.12 $H_2O$ | 0,02% |
| Potassium molybdate | 0,003% |
| Potassium glycerophosphate | 0,50% |
| Calcium lactate.5 $H_2O$ | 0,55% |
| Aluminum lactate | 0,35% |
| Magnesium lactate.3 $H_2O$ | 0,40% |
| Copper chloride | 0,001% |
| Water | ad 100% |

90% by weight of that composition are bottled with 10% by weight of a propellent mixture into aerosol cans.

We claim:

1. A skin care composition in the form of a cream, lotion, gel, emulsion, solution or aerosol spray comprising a mixture of salts selected from the group consisting of chlorides, sulphates, phosphates, citrates, lactates, glycerophosphates, gluconates, edetates, tartrates, malates, mandelates, benzoates, salicylates, phytates, cinnamates and amino acid salts, the improvement comprising a mixture of said salts in concentrations such that said composition comprises a mixture of cations in the following concentrations:
   Sodium: 0.01–5.0% by weight,
   Potassium: 0.01–3.0% by weight,
   Magnesium: 0.01–2.0% by weight,
   Calcium: 0.01–2.0% by weight, and
   Zinc: 0.01–1.0% by weight,
calculated on the total composition.

2. A skin care composition in the form of a cream, lotion, gel, emulsion, solution or aerosol spray comprising a mixture of salts selected from the group consisting of chlorides, sulphates, phosphates, citrates, lactates, glycerophosphates, gluconates, edetates, tartrates, malates, mandelates, benzoates, salicylates, phytates, cinnamates and amino acid salts, the improvement comprising a mixture of said salts in concentrations such that said composition comprises a mixture of cations in the following concentrations:
   Sodium: 0.01–5.0% by weight,
   Potassium: 0.01–3.0% by weight,
   Magnesium: 0.01–2.0% by weight,
   Calcium: 0.01–2.0% by weight,
   Zinc: 0.01–1.0% by weight, and
   Copper: 0.0001–0.01% by weight,
calculated on the total composition.

3. A skin care composition according to claim 1, wherein said composition comprises a mixture of cations in the following concentrations:
   Sodium: 0.1–2.5% by weight, Potassium: 0.1–1.5% by weight,
Magnesium: 0.1–1.0% by weight,
Calcium: 0.1–1.0% by weight, and
Zinc: 0.05–0.5% by weight,
calculated on the total composition.

4. A skin care composition according to claim 2, wherein said composition comprises a mixture of cations in the following concentrations:
Sodium: 0.1–2.5% by weight,
Potassium: 0.1–1.5% by weight,
Magnesium: 0.1–1.0% by weight,
Calcium: 0.1–1.0% by weight,
Zinc: 0.05–0.5% by weight, and
Copper: 0.0005–0.005% by weight,
calculated on the total composition.

5. A skin care composition according to claim 1, wherein said composition further contains vitamins.

6. A skin care composition according to claim 2, wherein said composition further contains vitamins.

7. A skin care composition according to claim 3, wherein said composition further contains vitamins.

8. A skin care composition according to claim 4, wherein said composition further contains vitamins.

9. A skin care composition according to claim 5, wherein said composition further contains at least one member selected from the group consisting of vitamin A, vitamin B, vitamin $B_2$, vitamin $B_6$, vitamin $B_{12}$, vitamin D, vitamin E, vitamin K, vitamin H, folic acid, nicotinamide, pantothenic acid and D-panthenol.

10. A skin care composition according to claim 6, wherein said composition further contains at least one member selected from the group consisting of vitamin A, vitamin B, vitamin $B_2$, vitamin $B_6$, vitamin $B_{12}$, vitamin D, vitamin E, vitamin K, vitamin H, folic acid, nicotinamide, pantothenic acid and D-panthenol.

11. A skin care composition according to claim 7, wherein said composition further contains at least one member selected from the group consisting of vitamin A, vitamin B, vitamin $B_2$, vitamin $B_6$, vitamin $B_{12}$, vitamin D, vitamin E, vitamin K, vitamin H, folic acid, nicotinamide, pantothenic acid and D-panthenol.

12. A skin care composition according to claim 8, wherein said composition further contains at least one member selected from the group consisting of vitamin A, vitamin B, vitamin $B_2$, vitamin $B_6$, vitamin $B_{12}$, vitamin D, vitamin E, vitamin K, vitamin H, folic acid, nicotinamide, pantothenic acid and D-panthenol.

13. A skin care composition according to claim 1, which is in the form of a cream and contains a mixture of salts in the following concentrations:
Sodium chloride: 0.2% by weight,
Potassium chloride: 0.1% by weight,
Calcium chloride: 0.04% by weight,
Magnesium sulfate: 0.05% by weight, and
Zinc sulfate: 0.025% by weight,
calculated on the total composition.

* * * * *